United States Patent [19]

Jensen

[11] 4,297,608
[45] Oct. 27, 1981

[54] MEASURING EQUIPMENT FOR ACOUSTIC DETERMINATION OF THE SPECIFIC GRAVITY OF LIQUIDS

[75] Inventor: Borge R. Jensen, Kobenhavn, Denmark

[73] Assignee: Danfoss A/S, Nordborg, Denmark

[21] Appl. No.: 145,620

[22] Filed: May 1, 1980

[30] Foreign Application Priority Data

May 10, 1979 [DK] Denmark .......................... 01924/79

[51] Int. Cl.³ .................................................. H01L 41/08
[52] U.S. Cl. .................................. 310/335; 73/32 A; 310/336
[58] Field of Search ................................ 310/334–336, 310/338; 73/452, 32 R, 32 A, 642, 602, 620, 589

[56] References Cited

U.S. PATENT DOCUMENTS

| | | | |
|---|---|---|---|
| 2,565,725 | 8/1951 | Frederick et al. | 310/335 X |
| 2,657,319 | 10/1953 | Smack | 310/335 |
| 2,711,646 | 6/1955 | Mendousse | 310/334 X |
| 2,869,357 | 1/1959 | Kritz | 73/32 |
| 3,028,749 | 4/1962 | Welkowitz | 73/32 A |
| 3,100,885 | 8/1963 | Welkowitz et al. | 73/32 X |
| 3,117,440 | 1/1964 | Wilner | 310/334 X |

*Primary Examiner*—Mark O. Budd
*Attorney, Agent, or Firm*—Wayne B. Easton

[57] ABSTRACT

The invention relates to a measuring probe for the acoustic determination of the specific gravity of a liquid. The probe includes a holder to which is attached at opposite ends thereof a ceramic piezoelectric transducer disc and a reflector disk. A reference element having a known acoustical impedance has one end thereof abutting the transducer disc and the other end thereof spaced from the reflector disc to form a sampling space therebetween.

1 Claim, 1 Drawing Figure

U.S. Patent  Oct. 27, 1981  4,297,608
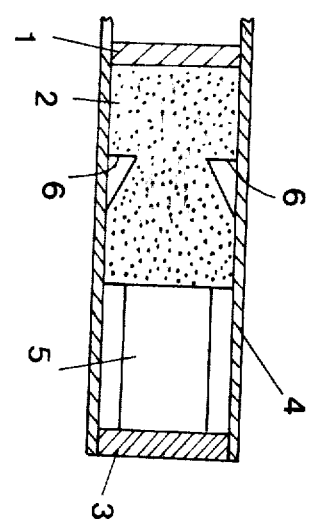

MEASURING EQUIPMENT FOR ACOUSTIC DETERMINATION OF THE SPECIFIC GRAVITY OF LIQUIDS

The present invention relates to a measuring equipment for determination of the specific gravity of liquids and of the kind stated in the introduction of the claim.

The acoustic impedance of a liquid is the product of the specific gravity of the liquid and the propagation time of an acoustic wave in the liquid. This connection is utilised in specific gravity determination in apparatus in which a transducer, e.g. a piezoelectric ceramic disc, transmits an ultrasonic pulse over a given distance through the liquid.

In measuring apparatus known so far this given distance is the distance between two walls of a measuring chamber, or twice that distance if the same transducer is used as both transmitter and receiver of the ultrasonic pulses. Such apparatus, e.g. known from the specifications of U.S. Pat. Nos. 3,028,749 and 2,926,522, require a relatively complicated and stationary measuring equipment.

According to the present invention, the transducer is suggested to be fitted in a measuring probe consisting of a tubular holder which also contains a reference unit which is in full contact with the transducer, and a reflection disc to be placed at some distance from the side of the reference unit which is opposite the one facing the transducer, and the tubular holder between the reference unit and the reflection disc to be slotted so that there is at least one opening in the tube wall, and the reference unit to have at least one all-round incision the limitation surface of which, facing the transducer, is parallel to the interface between the transducer and the reference unit.

Through this, a simple and mechanically stable measuring equipment is obtained, and it is easily portable because the measuring probe may be the size of an ordinary ball-point pen. Through the electronic circuit, the specific gravity of a liquid, in the space between the reference unit and the reflection disc, can be determined by measuring the reflector amplitude from the transition between the reference unit and the liquid and the propagation time of the acoustic wave in the liquid.

In the following, the invention will be explained in detail with reference to the drawing which shows a cross section of a measuring probe as specified in the invention, for acoustic determination of the specific gravity of liquids.

The probe shown consists of a piezoelectric ceramic disc (1), a reference unit (2) and a reflection disc (3), fitted in a tubular holder (4). Between the reference unit (2) and the reflection disc (3) the tubular holder (4) is slotted so that there is at least one opening (5) in the tube wall.

The ceramic disc (1) is connected to an electronic circuit—not shown in the drawing—which can apply electric pulses to the disc. Then, ultrasonic waves will be transmitted through the adjoining reference unit (2), pass through the open space between the reference unit (2) and the reflection disc (3), and be reflected to the ceramic disc. Here, the acoustic signals will be converted into electric signals which will be applied to the electronic circuit.

Thus, the ceramic disc (1) is used as both a transmitter and a receiver of acoustic pulses.

In the reference unit (2) there is an all-round slot, the limitation surface (6) of which faces the ceramic disc (1) and is parallel to the interface between the ceramic disc (1) and the reference unit (2), i.e. at right angles to the direction of sonic propagation in the reference unit (2).

When a short electric pulse is applied to the ceramic disc (1), an ultrasonic wave will be transmitted and propagated through the reference substance. Part of the sound will be totally reflected at the limitation surface (6) if, on the other side of the limitation surface (6), there is a substance, e.g. air, the acoustic impedance of which is a great deal lower than the acoustic impedance of the reference substance which may, e.g., be glass, aluminium or stainless steel. The amplitude of $A_o$ of the reflected echo will be proportional to the amplitude of the acoustic wave transmitted. The remaining acoustic wave transmitted will be propagated through the reference substance and be reflected to the interface between the reference unit (2) and the medium which has permeated through the opening (5) between the reference unit (2) and the reflection disc (3). Thus, if the measuring probe has been immersed in a liquid, the latter will be the substance adjoining the terminal surface of the reference unit (2).

From this terminal surface a sonic wave is reflected, the amplitude $A_1$ of which can be expressed as follows:

$$A_1 = A_i \frac{(\rho_r c_r - \rho_v c_v)}{(\rho_r c_r + \rho_v c_v)} \quad (1)$$

in which expression $A_i$ is the amplitude of the sonic wave transmitted, $\rho_r$ and $\rho_v$ designate the specific gravity of the reference unit and the liquid, and $c_r$ and $c_v$ the corresponding propagation times.

From the above expression (1) the specific gravity $\rho_v$ of the liquid can be calculated, because $$\rho_v = Z_r \frac{(A_i - A_1)}{(A_i + A_1) \times c_v} \quad (2)$$

in which expression $Z_r$ designates the given acoustic impedance $\rho_r c_r$ of the reference unit (2).

The part of the sonic wave which is not reflected by the interface between the reference unit (2) and the liquid, will be propagated through the latter and be reflected from the reflection disc to the ceramic disc (1). The propagation time in the liquid $c_v$ can be expressed as follows:

$$c_v = (2 \times l)/T_v \quad (3)$$

in which expression $l$ is the distance between the reference unit (2) and the reflection disc (3), and $T_v$ is the propagation time, determined by the time lag between the sonic waves reflected.

Through the amplitude $A_o$ the sound reflected from the limitation surface (6) the electronic circuit can adjust the transmission amplitude so that $A_i$ will be constant irrespective of variations of the temperature-variable data of the piezoelectric ceramic disc (1). On the basis of expressions (2) and (3) the specific gravity of the liquid can then be determined by measuring amplitude $A_1$, or the voltage $E_1$ proportional to that, and the propagation time $T_v$, because $$\rho_v = \frac{Z_r T_v (E_i - E_1)}{2 \times l (E_i + E_1)} \quad \text{where } E_i = \text{const.} \times A_i \quad (4)$$

Electronically, it may be difficult to get precise figures by analog multiplication and division of voltages, so the above expression (4) can be transcribed as follows:

$$\rho_v = \frac{T_v}{2 \times l} \times Z_{nor} + \frac{T_v}{2 \times l} \times \frac{(Z_r + Z_{nor})\left(\frac{Z_r - Z_{nor}}{Z_r + Z_{nor}} E_i - E_1\right)}{(E_i + E_1)} \quad (5)$$

in which expression $Z_{nor}$ is the acoustic impedance of a normal solution, for which purpose water at 20° centigrade will be expedient. If the probe is immersed in water, the second term of the above expression (5) will be zero, and the specific gravity is determined by measuring the time. As the acoustic impedance of most liquids is of the same size as that of water, the last term of expression (5) is of minor importance in the determination of the specific gravity. Consequently, any uncertainty in calculation of the last term will be negligible.

What is claimed is:

1. A measuring probe for the acoustic determination of the specific gravity of a liquid, comprising, a holder having a piezoelectric ceramic disc attached at one end thereof and a parallel arranged reflection disc attached at the other end thereof, a reference element having parallel end faces and a known acoustical impedance, said reference element having one of said end faces in abutting engagement with said piezoelectric disc and the other of said end faces in spaced relation to said reflection disc to form a sampling space therebetween, said reference element having an annularly shaped groove formed therein intermedite said end faces and having a planar surface adjacent to and parallel to said ceramic disc, said holder having wall means bounding and surrounding said annular groove, and said wall means forming an opening to provide ingress and egress to and from said sampling space for a medium externally of said probe.

* * * * *